United States Patent
Alshatwi et al.

(10) Patent No.: US 10,383,976 B1
(45) Date of Patent: Aug. 20, 2019

(54) METHOD OF FABRICATING NANOSTRUCTURES FROM FISH WASTE

(71) Applicant: KING SAUD UNIVERSITY, Riyadh (SA)

(72) Inventors: Ali A. Alshatwi, Riyadh (SA); Jegan Athinarayanan, Riyadh (SA); Vaiyapuri Subbarayan Periasamy, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 16/154,117

(22) Filed: Oct. 8, 2018

(51) Int. Cl.
| | |
|---|---|
| A61L 27/36 | (2006.01) |
| B82Y 5/00 | (2011.01) |
| A61K 35/60 | (2006.01) |
| C01B 32/15 | (2017.01) |
| B82Y 40/00 | (2011.01) |
| A61L 27/12 | (2006.01) |

(52) U.S. Cl.
CPC ......... *A61L 27/3608* (2013.01); *A61K 35/60* (2013.01); *A61L 27/12* (2013.01); *B82Y 5/00* (2013.01); *B82Y 40/00* (2013.01); *C01B 32/15* (2017.08); *A61L 2430/02* (2013.01)

(58) Field of Classification Search
CPC ......... A61L 27/3683; C01B 25/32; A61F 2/38
See application file for complete search history.

(56) References Cited

U.S. PATENT DOCUMENTS

| | | | |
|---|---|---|---|
| 9,403,688 B1 | 8/2016 | Alshatwi et al. | |
| 9,758,377 B2 * | 9/2017 | Iqbal | .............. C01B 25/32 |
| 2012/0251626 A1 | 10/2012 | Okada | |

FOREIGN PATENT DOCUMENTS

| | | |
|---|---|---|
| CN | 103705976 A | 4/2014 |
| CN | 104845618 A | 8/2015 |
| CN | 105905882 A | 8/2016 |
| CN | 106744808 A | 5/2017 |

OTHER PUBLICATIONS

Wu et al., Generation of nitrogen-doped photo luminescent carbonaceous nanodots via the hydrothermal treatment of fish scales for the detection of hypochlorite, May 12, 2015, RSC Adv, 2015, 5, pp. 44636-44641. (Year: 2015).*

Chai et al., Simple preparation of hydroxyapatite nanostructures derived from fish, Apr. 3, 2018, Materials Letters 222, pp. 156-159. (Year: 2018).*

Pon-On et al., Hydroxyapatite from fish scale for potential use as bone scaffold or regenerative material, Jan. 22, 2016, Materials Science and Engineering C 62, pp. 183-189. (Year: 2016).*

(Continued)

*Primary Examiner* — Brian A Dukert
(74) *Attorney, Agent, or Firm* — Richard C. Litman

(57) ABSTRACT

The fabrication of nanostructures from fish waste is a method of co-fabricating C-dots and hydroxyapatite from fish scales. The method includes hydrothermal treatment of fish scales to simultaneously produce hydroxyapatite nanostructures and C-dot nanostructures. The C-dots may be used as probes for fluorescent imaging. The hydroxyapatite nanostructures may be used for tissue engineering applications.

7 Claims, 7 Drawing Sheets

(56) References Cited

OTHER PUBLICATIONS

Zhang et al., Carbon dots: large-scale synthesis, sensing and bioimaging, Sep. 2016, Materials Today, vol. 19, No. 7, pp. 382-393. (Year: 2016).*
Mustafa et al., "Hydroxyapatite Extracted from Waste Fish Bones and Scales via Calcination Method," Applied Mechanics and Materials, vols. 773-774, pp. 287-290, Jul. 15, 2015.
Kongsri et al., "Nanocrystalline hydroxyapatite from fish scale waste: preparation, characterization and application for selenium adsorption in aqueous solution," Chemical Engineering Journal, vols. 215-216, pp. 522-532, Jan. 15, 2013.
Wu et al., "Generation of nitrogen-doped photoluminescent carbonaceous nanodots via the hydrothermal treatment of fish scales for the detection of hypochlorite," RSC Advances, 5, 44636-44641, May 12, 2015.
Pon-On et al., "Hydroxyapatite from fish scale for potential use as bone scaffold or regenerative material," Materials Science and Engineering: C, vol. 62, pp. 183-189, May 1, 2016.
Sunil et al., "Producing hydroxyapatite from fish bones by heat treatment," Materials Letters, vol. 185, pp. 411-414, Dec. 15, 2016.

\* cited by examiner

METHOD OF FABRICATING NANOSTRUCTURES FROM FISH WASTE

BACKGROUND

1. Field

The disclosure of the present patent application relates to nanotechnology, and particularly to fabrication of nanostructures from fish waste.

2. Description of the Related Art

Biomaterials derived from naturally occurring resources have been employed to design scaffolds for biomedical applications. Naturally available biomaterials are readily available, eco-friendly, biocompatible, biodegradable and cost-effective. Several attempts have been made to derive biomaterials such as collagen, keratin, cellulose, hyaluronic acid, chitin, chitosan, pectin, calcium phosphate and biogenic silica from natural sources. For instance, collagen scaffolds have been derived from jellyfish. Hyaluronic acid has been extracted from egg shells using a sequential process. Higher molecular mass hyaluronic acid has been extracted from *Aetobatus narinari* liver. Chitin and chitosan were isolated from *Penaeus kerathurus* waste, *Carcinus mediterraneus* shells, and *Sepia officinalis*. Aquatic invertebrates including *Ranatra linearis, Anax imperator, Hydrophilus piceus, Notonecta glauca, Agabus bipustulatus*, and *Asellus aquaticus* have been used as precursors for chitin and chitosan production. Further, biogenic silica nanostructures have been produced from rice husk, sugarcane and millet.

The fish industry produces large quantities of waste materials during fish processing. Every year 18 to 30 million tons of fish waste are generated worldwide. Fish waste is a hazardous waste that displays high chemical oxygen demand and biological oxygen demand, while acting as a source of pathogenic microbes. The management of fish waste is a significant global challenge.

Thus, a method for fabrication of nanostructures from fish waste solving the aforementioned problems is desired.

SUMMARY

A method for fabricating nanostructures from fish waste includes treating fish scales using a single hydrothermal process to simultaneously produce two distinct nanostructures, carbon dots (C-dots) and hydroxyapatite. The C-dots are in a liquid fraction and the hydroxyapatite is produced as a solid residue. In an embodiment, the C-dots may be used as probes for fluorescent imaging. In an embodiment, the hydroxyapatite nanostructures may be used for tissue engineering applications.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1A:
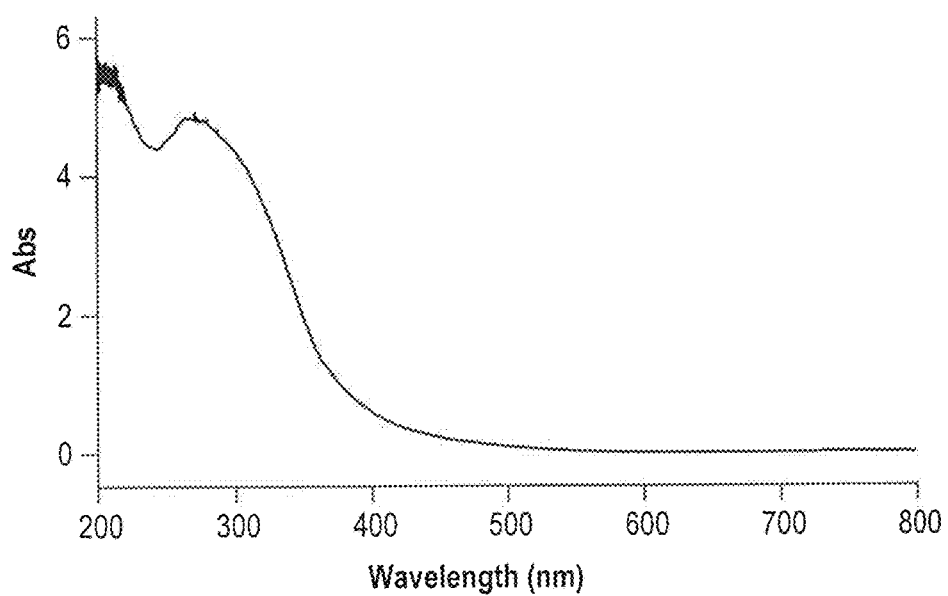
FIG. 1A depicts a graph of the ultraviolet visible absorbance spectrum of the fish scale derived C-dots according to the present teachings.

A method of preparing nanostructures from fish waste involves treating fish scales using a single hydrothermal process to simultaneously produce two distinct nanostructures, carbon dots (herein, "C-dots") and hydroxyapatite. The hydrothermal treatment can be conducted at a temperature of about 280° C. For example, fish scales can be mixed with water to form a mixture and the mixture can be maintained in a hydrothermal autoclave at a temperature of about 280° C. for about three hours to provide a heated mixture including both C-dots and hydroxyapatite nanostructures. After the hydrothermal treatment, the nanostructures may be separated by filtration. The isolated solids may include the hydroxyapatite nanostructures. The isolated liquids may include the C-dot nanostructures.

As fish scale includes chitin, hydroxyapatite, and collagen, fish scale is an excellent resource for different kinds of materials. In an embodiment, the fabricated C-dots may be used as fluorescent probes for cellular imaging. For example, the fabricated C-dots may be used as fluorescent probes for cellular imaging of stem cells. In an embodiment, the fabricated hydroxyapatite nanoparticles may be used as a scaffold for bone tissue engineering applications. The fish scale derived hydroxyapatite scaffold can be a suitable platform for multi-layer cell cultures, cell-based assay models, high-throughput drug screening, cell-replacement therapies, stem cell differentiation, and large scale cell production for tissue engineering applications. In an embodiment, the fabrication of nanostructures from fish waste may include use of any kind of fish scale.

As described herein, the fabricated nanostructures were characterized using X-ray diffractometer (XRD), Fourier-transform infrared spectroscopy (FTIR), scanning electron microscopy (SEM), and transmission electron microscopy (TEM). The fabricated nanostructures demonstrated good biocompatibility in in vitro cytotoxicity assays. The fabricated C-dots are spherical and range from about 3 nm to about 15 nm in diameter. The C-dots exhibit excitation dependent photoluminescence.

The following examples further illustrate the present teachings.

Example 1

Co-Fabricating Nanostructures

Fish scales were obtained from a fish market in Riyadh, Saudi Arabia, washed with water and dried. Five grams of dried fish scales were mixed with 250 mL MilliQ water. The mixture was transferred to a hydrothermal autoclave and held at 280° C. for 3 h. The resulting liquid and solid portions were then separated by filtration. The liquid portion, including C-dots, was purified by dialysis and freeze-dried for further analysis. The separate white solid portion included hydroxyapatite nanostructures and a small quantity of organic substances.

Example 2

C-Dot Optical Properties

The optical properties of the fabricated C-dots were analyzed using ultraviolet-visible spectroscopy and fluorescent spectroscopy. XRD patterns were analyzed using an X-ray diffractometer (Bruker diffractometer, Model D8 Advance) and Cu Kα radiation with 40 kV and 100 mA current. The size and shape of C-dots was determined using TEM (JEOL, Tokyo, Japan) with an accelerating voltage of 200 kV. Dried samples were dispersed in an aqueous solution under ultra-sonication and coated on carbon-coated copper grid for TEM analyses. The FTIR spectra (4000-600 $cm^{-1}$) of the samples were recorded using a Nicolet 5700 spectrometer.

Figure 1B:
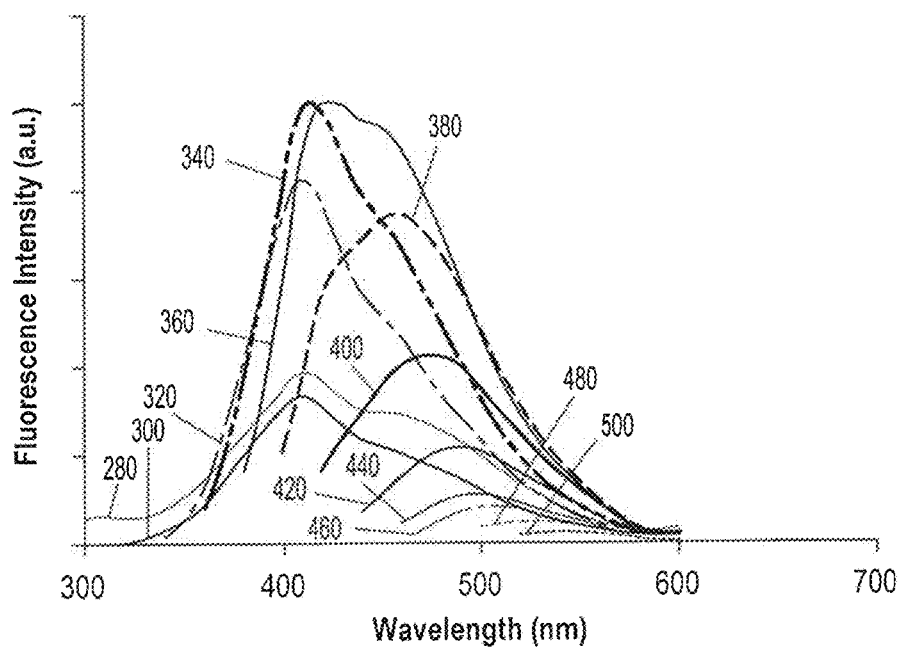
FIG. 1B depicts a graph of the fluorescent spectra of the fish scale derived C-dots at difference excitation wavelengths.

FIG. 1A depicts a UV-vis spectrum of fish scale derived C-dots. The spectrum exhibits a sharp peak at 280 nm, which is attributable to the n-π* transition of the carbonyl groups. The C-dots emit bright blue fluorescence under UV light excitation at $\lambda_{ex}$=365 nm. The fluorescence behaviors of the synthesized C-dots were investigated by changing the excitation wavelength from 280 nm to 520 nm. FIG. 1B depicts a graph of the fluorescence spectra of fish scale derived C-dots, demonstrating that these C-dots display excitation dependent emission peaks. Increased excitation wavelength results in decreased fluorescence intensity.

Figure 1C:
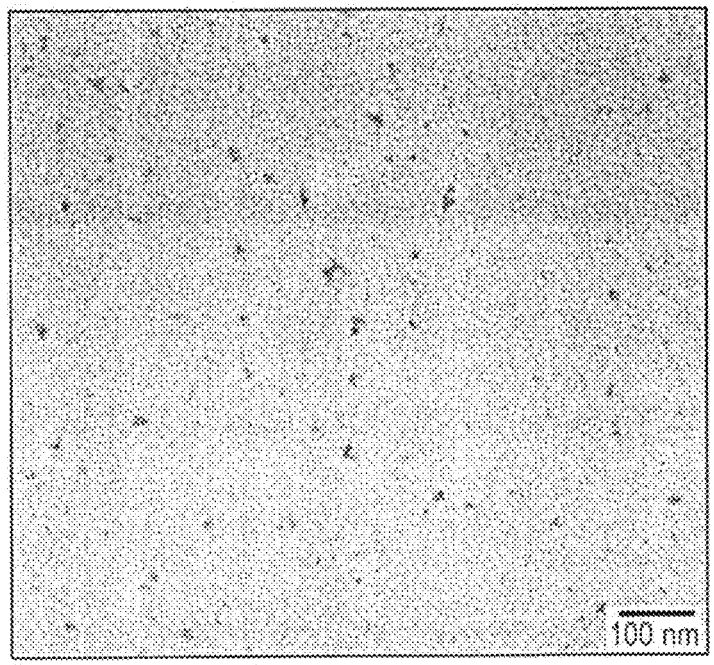
FIG. 1C depicts a transmission electron micrograph of the fish scale derived C-dots.
Figure 1D:
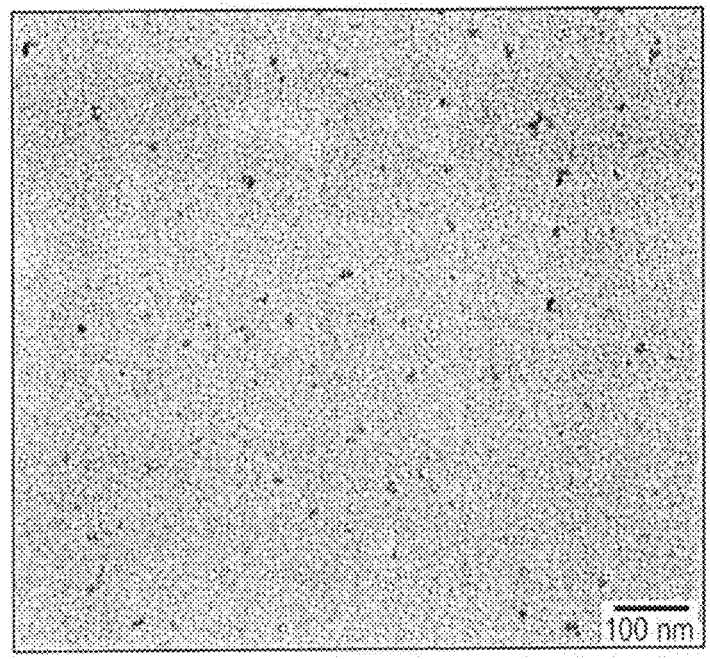
FIG. 1D depicts a transmission electron micrograph of the fish scale derived C-dots.
Figure 1E:
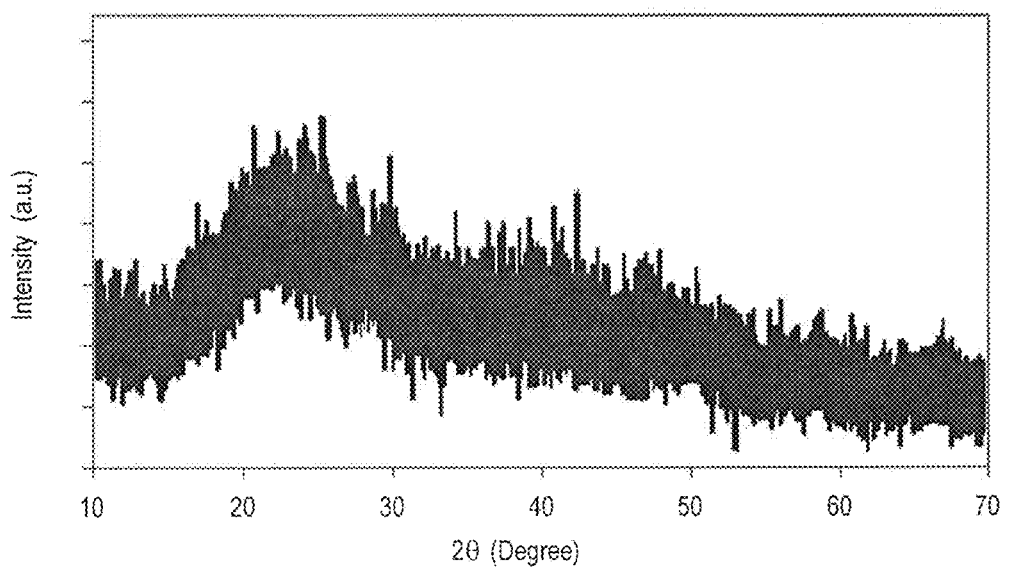
FIG. 1E depicts an energy dispersive X-ray spectrograph of the fish scale derived C-dots.

The structure and morphology of the synthesized C-dots was analyzed using transmission electron microscopy. As shown in FIGS. 1C and 1D, TEM imaging reveals that the C-dots are well dispersed, spherical in shape, and about 3-15 nm in diameter. As shown in FIG. 1E, the XRD spectra of fish derived C-dots shows a broad peak at 23° of 2 theta value, corresponding to amorphous carbon.

Example 3

Structure of Hydroxyapatite Nanoparticles

Figure 2:
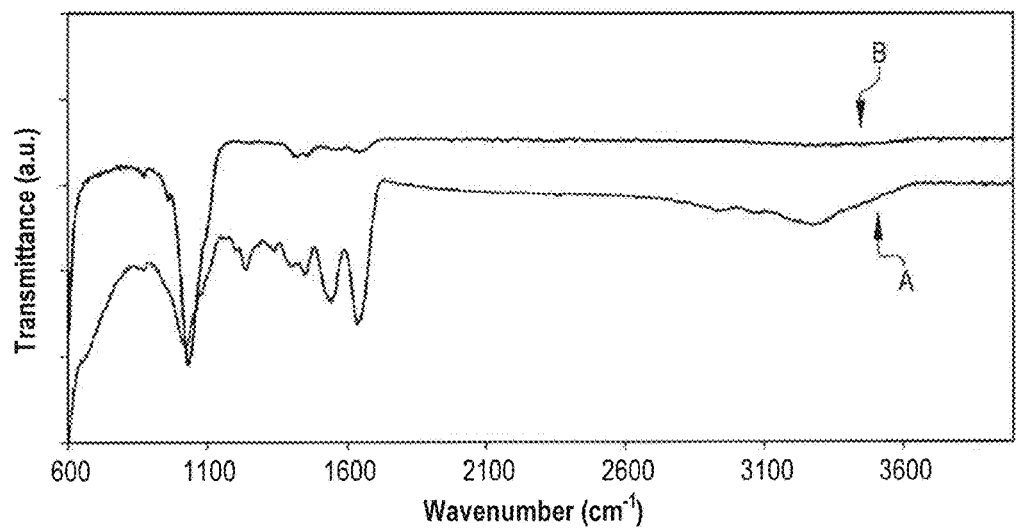
FIG. 2 depicts the fourier-transform infrared spectra of (A) the fish scale derived C-dots and (B) the fish scale derived hydroxyapatite at 280 degrees Celsius.

The fish scale derived solid fraction (hydroxyapatite nanoparticle) functional groups were analyzed using FTIR. FIG. 2 depicts the FTIR spectra of fish scale and fish scale derived hydroxyapatite nanoparticles. FTIR of the source fish scales displays a number of absorption bands at 3285, 3061, 2926, 1633, 1531, 1437, 1395, 1333, 1280, 1233, 1195, 1066, 1019, 876 and 656 $cm^{-1}$, which correspond to chitosan, collagen and hydroxyapatite. The peaks at 1633, 1531 and 1280 $cm^{-1}$ are attributed to amide I, amide II and amide III groups respectively, due to the presence of collagen and chitosan in the fish scales. Additionally, the peaks at 1437, 1019 and 876 $cm^{-1}$ are attributed to phosphate groups due to the presence of hydroxyapatite. The FTIR spectrum confirms that fish scales contains chitosan, collagen and hydroxyapatite.

The fish scale derived hydroxyapatite nanoparticles exhibited various absorption peaks around 632, 962, 1032 and 1089 $cm^{-1}$ confirming the presence of hydroxyapatite. The peaks at 632, 962, 1033 and 1089 $cm^{-1}$ are attributed to P-O stretching vibration of hydroxyapatite nanoparticles.

Figure 3A:
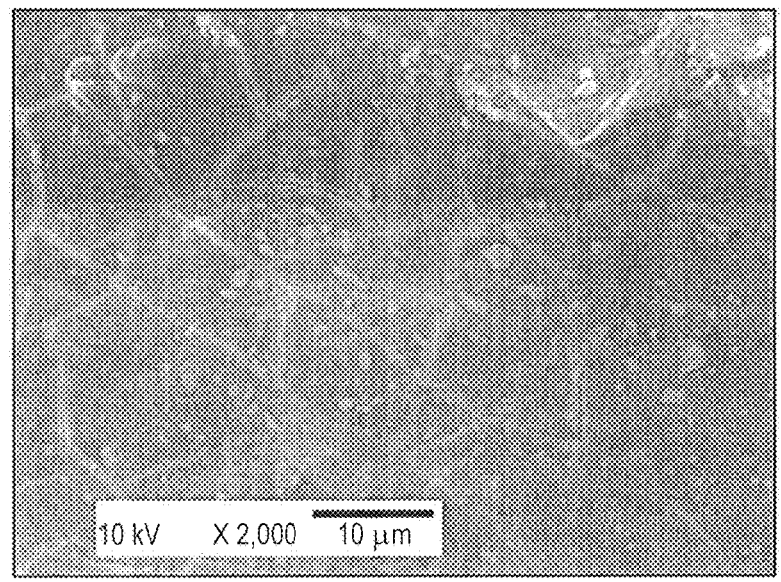
FIG. 3A depicts a scanning electron micrograph of fish scales.
Figure 3B:
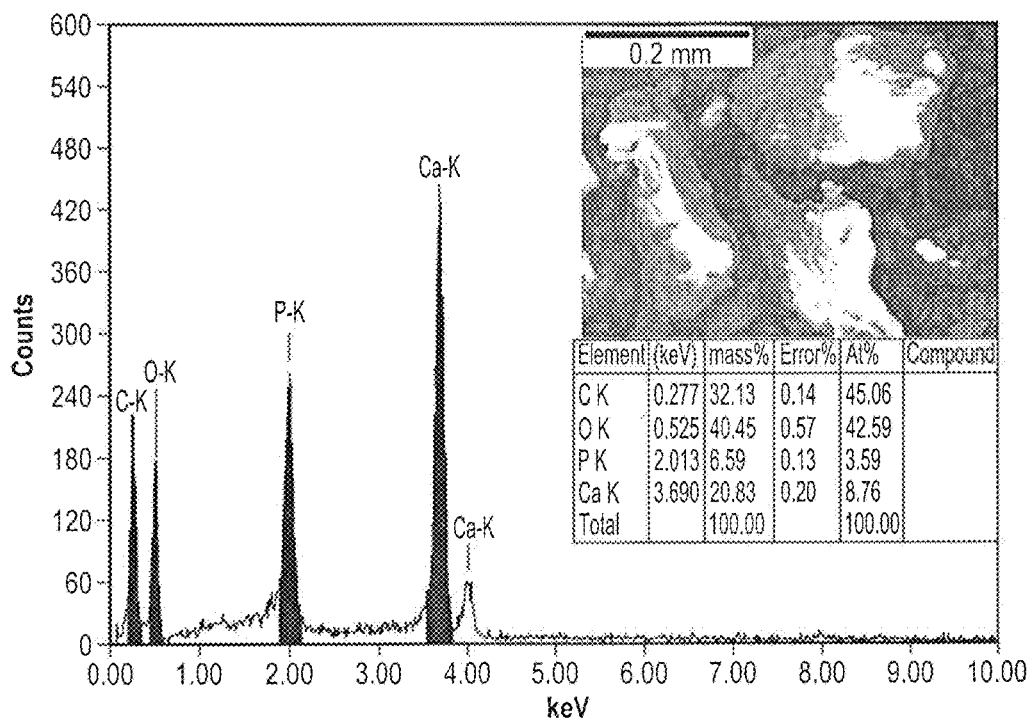
FIG. 3B depicts an energy dispersive X-ray spectrograph of fish scales.
Figure 3C:
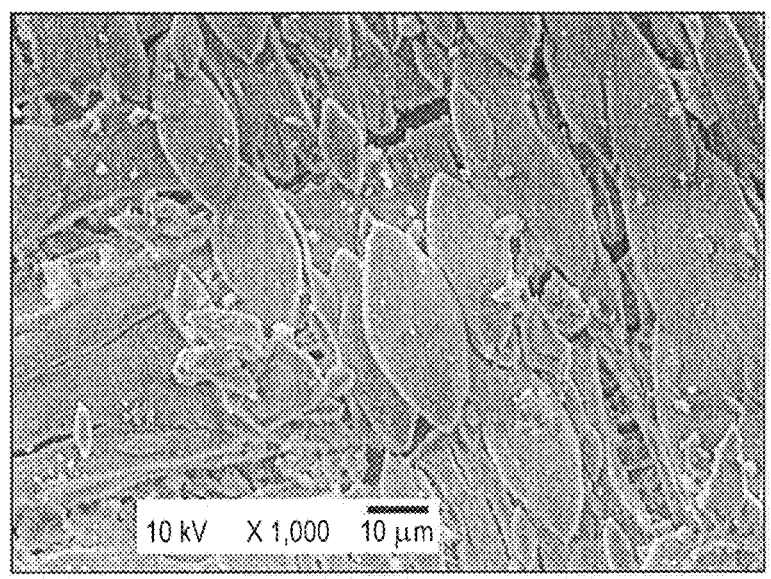
FIG. 3C depicts a scanning electron micrograph of the fish scale-derived hydroxyapatite nanostructures according to the present teachings.
Figure 3D:
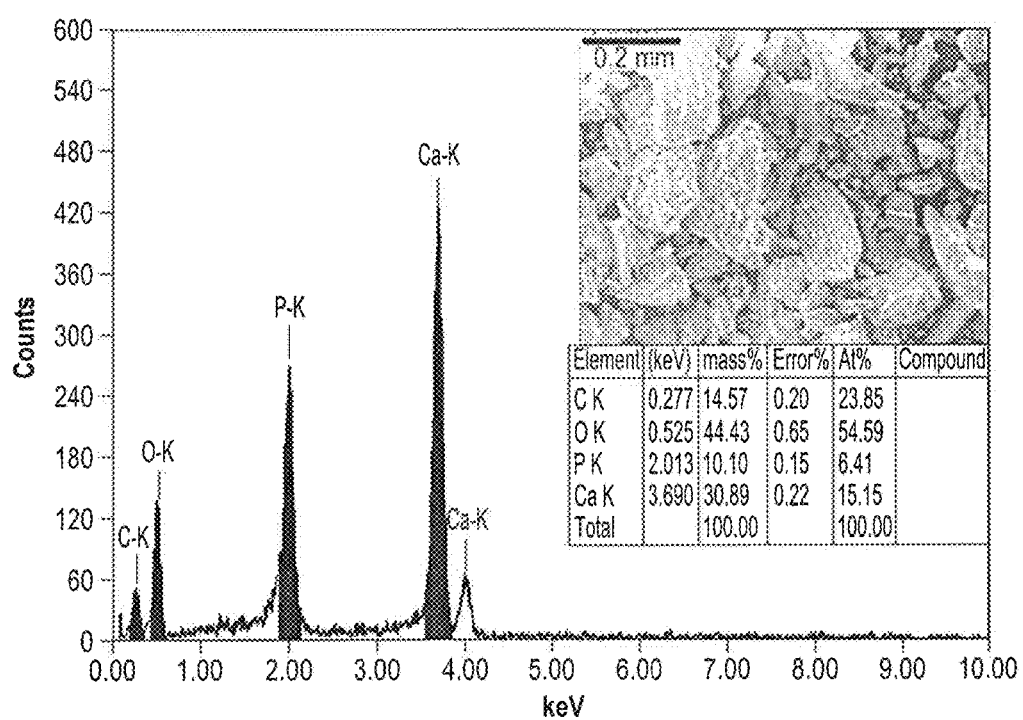
FIG. 3D depicts an energy dispersive X-ray spectrograph of fish scale derived hydroxyapatite nanostructures.

FIGS. 3A-3D depict SEM images and corresponding EDS spectra of fish scales (FIGS. 3A-3B) and of fish scale derived hydroxyapatite nanostructures (FIGS. 3C-3D). FIGS. 3C-3D further demonstrate that the fish scale derived nanostructures contain calcium and phosphate ions, confirming that the fish scale derived materials are hydroxyapatite nanostructures.

Example 4

Nanostructure Biocompatibility

The effect of synthesized nanostructures (C-dots and hydroxyapatite) on human mesenchymal stem cell (hMSC) viability was assessed using the MTT (3-(4,5-dimethylthi-azol-2-yl)-2,5-diphenyltetrazolium bromide) assay. HMSCs were grown in DMEM with 10% FBS and maintained at 5% $CO_2$ and at 37° C. in a $CO_2$ incubator. Cells were plated at a density of 10,000 cells per well in 96 well plates. After 24 hours, the cells were treated with various concentrations of synthesized nanostructures for 24 hours or 48 hours. Next, the nanostructure exposed cells were incubated with 20 μL MTT dye (5 mg/mL) per well at 37° C. overnight. The supernatant was removed from each well and 100 μl DMSO was added to each well to dissolve the purple colored formazan crystals. The plates were monitored in a microplate reader (glomax) at 570 nm (measurement filter). The percentage of viable cells was calculated using Formula 1:

$$\text{Cell viability}(\%) = \frac{\text{Mean } OD \text{ Untreated Cells(Control)} - \text{Mean } OD \text{ Treated Cells}}{\text{Mean } OD \text{ Untreated Cells}} \times 100 \quad \text{FORMULA 1}$$

Figure 4A:
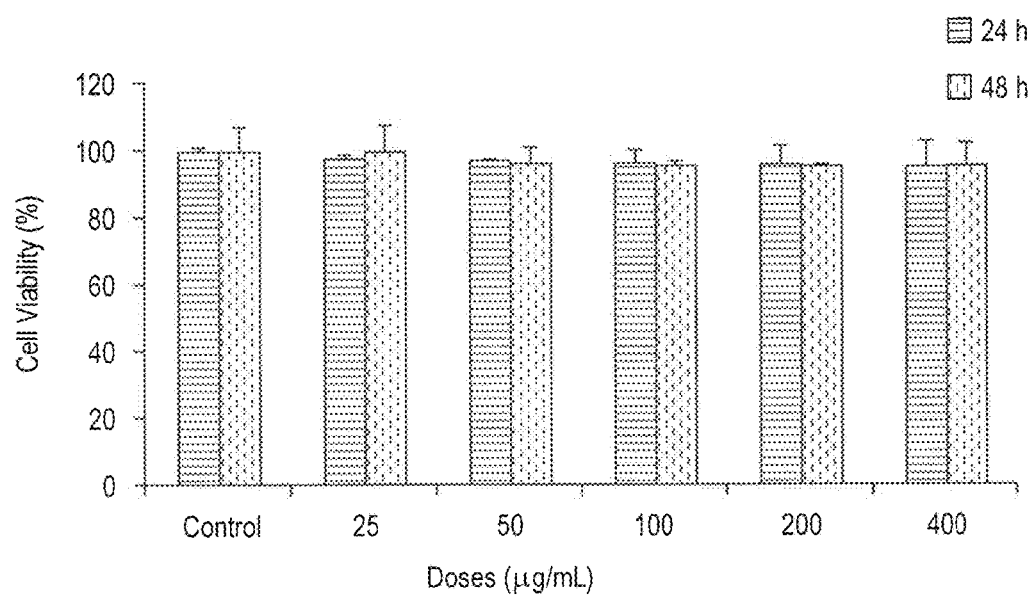
FIG. 4A depicts a graph of human mesenchymal stem cell viability when treated with varying doses of fish scale derived C-dots.
Figure 4B:
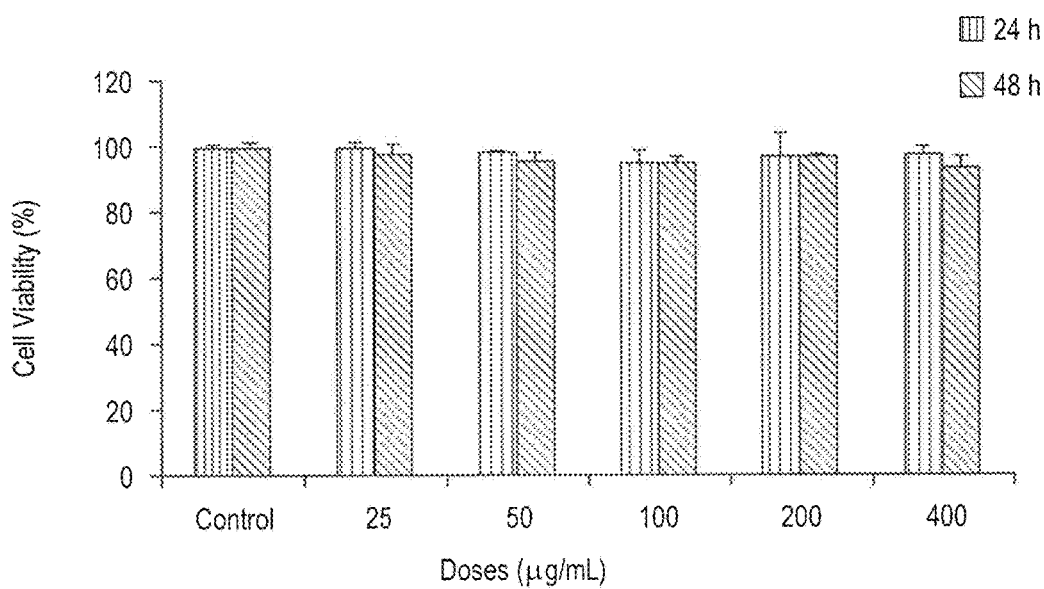
FIG. 4B depicts a graph of human mesenchymal stem cell viability when treated with varying doses of fish scale derived hydroxyapatite nanostructures.

As shown in FIGS. 4A-4B, doses from 25 μg/ml to 400 μg/ml of the synthesized nanostructures did not reduce the cell viability of hMSCs.

Example 5

Nanostructure Effect on Nuclear Architecture

The synthesized nanostructures influence on nuclear architecture was assessed. Acridine orange/ethidium bromide (AO/EB) staining and Hoechst staining methods were used to assess nuclear morphology. HMSCs were grown in 12 well plates and after 80-90% confluence, these cells were exposed to different concentrations of fabricated nanostructures for 24 hours and 48 hours. After incubation, the cells were washed with phosphate buffer saline and stained with AO/EB dual stain or Hoechst stain. After staining, the cells were observed under fluorescence microscopy.

These nuclear morphology studies confirmed that the synthesized nanostructures are non-toxic and biocompatible to hMSCs.

Example 6

Nanostructure Applications

The C-dots were applied to labelling and bio-imaging of cells. Cell morphology was observed under confocal fluorescence microscopy with different excitations such as 405 nm, 480 nm, and 568 nm. C-dots were observed in the cell membrane and cytoplasmic regions.

Synthesized hydroxyapatite nanostructures were also used in osteogenic differentiation for bone tissue engineering.

It is to be understood that the method for fabrication of nanostructures from fish waste is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method for co-fabricating nanostructures from fish scales comprising:
   suspending fish scales in water to produce a mixture;
   autoclaving the mixture to provide a heated mixture;
   filtering the heated mixture to provide a liquid portion and a solid portion; and
   freeze-drying the liquid portion;
   wherein the solid portion includes hydroxyapatite nanostructures and the liquid portion includes carbon dot nanostructures.

2. The method for co-fabricating nanostructures from fish scales according to claim 1, wherein 5 grams of fish scales are suspended in water.

3. The method for co-fabricating nanostructures from fish scales according to claim 1, wherein the mixture is autoclaved for 3 hours at 280° C.

4. Carbon dots prepared according to the method of claim 1, the carbon dots having a size ranging from about 3 nm to about 15 nm in diameter.

5. A method of cellular imaging, comprising contacting cells with the carbon dots of claim 4 and using an imaging method to observe the cellular morphology of the cells.

6. A method for co-fabricating nanostructures from fish scales comprising:
   suspending fish scales in water to produce a mixture;
   autoclaving the mixture for 3 hours at 280° C. to provide a heated mixture; and
   filtering the heated mixture to provide a liquid portion and a solid portion;
   wherein said solid portion includes hydroxyapatite nanostructures and said liquid portion includes carbon dot nanostructures.

7. The method of claim 6, wherein the carbon dots have a size ranging from about 3 nm to about 15 nm in diameter.

\* \* \* \* \*